United States Patent
Kao et al.

(10) Patent No.: US 11,446,280 B2
(45) Date of Patent: **\*Sep. 20, 2022**

(54) COMPOUNDS AND METHODS FOR THE TREATMENT OF MICROBIAL INFECTIONS

(71) Applicant: Versitech Limited, Hong Kong (CN)

(72) Inventors: Yi Tsun Richard Kao, Hong Kong (CN); Peng Gao, Hong Kong (CN); Xuechen Li, Hong Kong (CN); Ming Liu, Hong Kong (CN)

(73) Assignee: VERSITECH LIMITED, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/679,313

(22) Filed: Nov. 11, 2019

(65) Prior Publication Data

US 2020/0069642 A1    Mar. 5, 2020

Related U.S. Application Data

(62) Division of application No. 16/041,836, filed on Jul. 22, 2018, now Pat. No. 10,471,045.

(60) Provisional application No. 62/535,540, filed on Jul. 21, 2017.

(51) Int. Cl.
| | |
|---|---|
| *A61K 31/40* | (2006.01) |
| *A61K 31/496* | (2006.01) |
| *A61K 31/47* | (2006.01) |
| *A61K 31/454* | (2006.01) |
| *A61K 31/4453* | (2006.01) |
| *A61K 31/444* | (2006.01) |
| *A61K 31/4406* | (2006.01) |
| *A61K 31/4402* | (2006.01) |
| *A61K 31/404* | (2006.01) |
| *A61K 31/18* | (2006.01) |
| *A61K 31/167* | (2006.01) |
| *A61K 31/357* | (2006.01) |
| *A61P 31/04* | (2006.01) |
| *C07D 317/60* | (2006.01) |
| *C07D 295/26* | (2006.01) |

(52) U.S. Cl.
CPC ............ *A61K 31/40* (2013.01); *A61K 31/167* (2013.01); *A61K 31/18* (2013.01); *A61K 31/357* (2013.01); *A61K 31/404* (2013.01); *A61K 31/4402* (2013.01); *A61K 31/444* (2013.01); *A61K 31/4406* (2013.01); *A61K 31/4453* (2013.01); *A61K 31/454* (2013.01); *A61K 31/47* (2013.01); *A61K 31/496* (2013.01); *A61P 31/04* (2018.01); *C07D 295/26* (2013.01); *C07D 317/60* (2013.01)

(58) Field of Classification Search
None
See application file for complete search history.

(56) References Cited

FOREIGN PATENT DOCUMENTS

| CN | 102795953 B | 5/2015 |
|---|---|---|
| WO | 2010123599 A2 | 10/2010 |

OTHER PUBLICATIONS

Chemical Abstract Registry No. 1303107-35-8, indexed in the Registry File on STN CAS Online May 31, 2011.*
Chemical Abstract Registry No. 514808-63-0, indexed in the Registry File on STN CAS Online May 14, 2003.*
Chemical Abstract Registry No. 496032-89-4, indexed in the Registry File on STN CAS Online Feb. 28, 2003.*
Federal Register, vol. 72, No. 161, Aug. 21, 2007, p. 46722.*
Chemical Abstract Registry No. 587845-78-1, indexed in the Registry File on STN CAS Online Sep. 18, 2003.*
Chemical Abstract Registry No. 1014250-03-3, indexed in the Registry File on STN CAS Online Apr. 13, 2008.*
Chemical Abstract Registry No. 1303294-50-9, indexed in the Registry File on STN CAS Online May 31, 2011.*
Chemical Abstract Registry No. 1091545-67-3, indexed in the Registry File on STN CAS Online Dec. 29, 2008.*
Chemical Abstract Registry No. 1182540-23-3, indexed in the Registry File on STN CAS Online Sep. 11, 2009.*
Chemical Abstract Registry No. 1182469-00-6, indexed in the Registry File on STN CAS Online Sep. 11, 2009.*

(Continued)

*Primary Examiner* — Po-Chih Chen
(74) *Attorney, Agent, or Firm* — Idea Intellectual Limited; Margaret A. Burke; Sam T. Yip

(57) ABSTRACT

Provided herein are compounds, derivatives thereof, and compositions including one or more of the compounds and derivatives, and methods for prevention and/or treatment of microbial infections and/or related diseases or conditions. The present compounds and/or derivatives thereof can be represented by Formula (I):

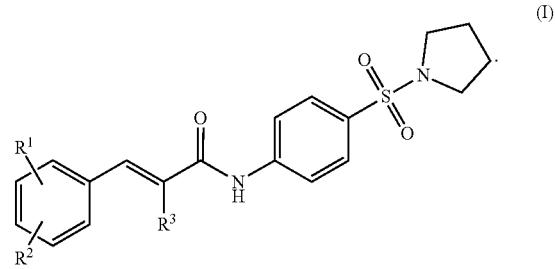

The present methods include administering to a subject an effective amount of one or more compounds of Formula (I). In one embodiment, the microbial infections are bacterial infections. More specifically, the bacterial infections are staphylococcal infections.

10 Claims, 7 Drawing Sheets
(1 of 7 Drawing Sheet(s) Filed in Color)

(56) References Cited

OTHER PUBLICATIONS

Chemical Abstract Registry No. 760960-07-4, indexed in the Registry File on STN CAS Online Oct. 12, 2004.*
Chemical Abstract Registr No. 939542-33-3, indexed in the Registry File on STN CAS Online Jun. 27, 2007.*
Chemical Abstract Registr No. 895692-81-6, indexed in the Registry File on STN CAS Online Jul. 25, 2006.*
Extended search report of corresponding European Patent Application No. 18835480.7 dated Feb. 3, 2021.
Sania Marwaha et al., "N-Acylated Derivatives of Sulfamethoxazole and Sulfafurazole Inhibit Intracellular Growth of Chlamydia trachomatis", Antimicrobial Agents and Chemotherapy, 2014,vol. 58, No. 5, p. 2968-2971.
Ajeet et.al., "Synthesis, Spectral Characterization, Docking Studies and QSAR Screening of 4-amino-benzenesulfonamides/N-acetyl 4-amino-benzenesulfonamide Derivatives as Antimicrobial Agents", Journal of Pharmacy and Nutrition Sciences, 2014, 4, p. 135-153.
Youxin Wang et.al., "Discovery of Potent Benzofuran-Derived Diapophytoene Desaturase (CrtN) Inhibitors with Enhanced Oral Bioavailiability for the Treatment of Methicillin-Resistant *Staphylococcus aureus* (MRSA) Infections", Journal of Medicinal Chemistry, 2016, vol. 59, No. 7, p. 3215-3230.
Chemical Abstract Registry No. 315671-53-5, indexed in the Registry File on STN CAS Online Jan. 22, 2001.
Chemical Abstract Registry No. 600124-13-8, indexed in the Registry File on STN CAS Online Oct. 7, 2003.
Chemical Abstract Registry No. 521295-01-2, indexed in the Registry File on STN CAS Online May 28, 2003.
Chemical Abstract Registry No. 1182519-48-7, indexed in the Registry File on STN CAS Online Sep. 11, 2009.
Chemical Abstract Registry No. 590399-18-1, indexed in the Registry File on STN CAS Online Sep. 22, 2003.
Chemical Abstract Registry No. 356100-60-2, indexed in the Registry File on STN CAS Online Sep. 12, 2001.
Chemical Abstract Registry No. 497089-89-1, indexed in the Registry File on STN CAS Online Mar. 6, 2003.
Chemical Abstract Registry No. 895692-73-6, indexed in the Registry File on STN CAS Online Jul. 25, 2006.
Chemical Abstract Registry No. 895689-82-4, indexed in the Registry File on STN CAS Online Jul. 25, 2006.
Chemical Abstract Registry No. 895689-74-4, indexed in the Registry File on STN CAS Online Jul. 25, 2006.
Chemical Abstract Registry No. 648911-93-7, indexed in the Registry File on STN CAS Online Feb. 11, 2004.
Examination report of corresponding Australian Patent Application No. 2018304613.

* cited by examiner

COMPOUNDS AND METHODS FOR THE TREATMENT OF MICROBIAL INFECTIONS

CROSS-REFERENCE TO RELATED APPLICATIONS

The present application is a division of the U.S. non-provisional patent application Ser. No. 16/041,836 filed Jul. 22, 2018, which claims priority from a U.S. provisional patent application Ser. No. 62/535,540 filed Jul. 21, 2017, and the disclosures of which are incorporated by reference in their entirety.

TECHNICAL FIELD

The present invention relates to compounds and derivatives thereof, composition comprising said compounds and/or derivatives, and methods for treating microbial infections and/or related diseases or conditions. More specifically, the present compounds, derivatives, composition comprising thereof, and methods are for bacterial infections.

BACKGROUND OF THE INVENTION

*Staphylococcus aureus* is a major human pathogen in communities and hospitals, causing a variety of infections that ranges from harmless infections to life threatening conditions [18]. With the wide-spread dissemination of methicillin-resistant *S. aureus* (MRSA) in hospitals and in communities, treating *S. aureus* associated infections has become increasingly difficult [19]. Staphyloxanthin has been proven to be an important factor in promoting bacterial invasion [1]. Five genes, crtOPQMN, located in an operon are responsible for the biosynthesis of the pigment. The transcription of the operon is driven by a $\sigma^B$-dependent promoter upstream of crtO, and ends with a terminator downstream of crtN [2]. The pigments that endow *S. aureus* with a golden color also make it resistant to attack from reactive oxygen species (ROS) and neutrophils [3]. Pigmented bacteria have increased resistance to the host's immune defenses [4].

In a mouse subcutaneous model of infection, animals infected with a wild-type strain of *S. aureus* had higher bacterial loads and larger visible lesions than those infected with non-pigmented bacteria [4]. The reduced virulence of bacterial strains with defective carotenoid synthesis was also shown in a mouse systemic *S. aureus* infection model [3]. In vitro and in vivo data suggest that blocking pigment synthesis may reduce pathogenicity.

Dehydrosqualene synthase (CrtM) catalyses the first step of the biosynthetic pathway, was shown to be a target for anti-infective therapy based on virulence factor neutralization. Diphenylamine was found to be an inhibitor of 4,4-diapophytoene desaturase (CrtN) at high micromolar level [5]. Another potential inhibitor of CrtN, naftifine, a FDA approved antifungal compound was shown to reduce bacterial load in different mice infection models [6]. However, there remains a need for new compounds and methods of treatment for staphylococcal infections.

SUMMARY OF THE INVENTION

Provided herein are compounds and methods for prevention and/or treatment of microbial infections and/or related disease or conditions. In a first aspect, the present invention provides compounds and/or their derivatives which can be represented by Formula (I):

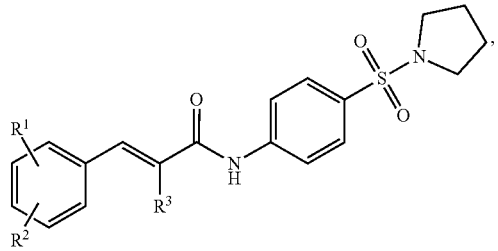

where $R^1$, $R^2$, and $R^3$ can independently or jointly be selected from the group: H; F; Cl; Br; I; OH; CN; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers thereof; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid (—$SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (=O); ether (—$OR^4$); and ester (—$COOR^5$ and —OC(=O)$R^5$);

where $R^1$ and $R^2$ can be bonded together to form a four-, five-, or six-membered heterocyclyl, cycloalkenyl, or cycloalkyl; and where $R^4$ and $R^5$ can be independently or jointly selected from the group consisting of: $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl.

In one embodiment, the present compounds and/or the derivatives thereof can be an anti-virulent agent for bacteria.

In another embodiment, the present compounds and/or the derivatives thereof are effective in reducing virulence of bacteria.

In other embodiment, the bacteria that the present compounds and/or the derivatives thereof are effective in reducing their virulence comprise *Staphylococci* sp.

In yet another embodiment, the bacteria that the present compounds and/or the derivatives thereof are effective in reducing their virulence comprise *Staphylococcus aureus* (*S. aureus*).

In still another embodiment, the bacteria that the present compounds and/or the derivatives thereof are effective in reducing their virulence comprise methicillin-resistant *S. aureus* (MRSA).

In other embodiment, said reducing the virulence of bacteria by the compounds and/or derivatives thereof comprises inhibiting biosynthesis of staphyloxanthin in said bacteria and/or inhibiting or reducing production of pigments that are resistant to the bacterial host's immune defenses.

A composition for preventing and/or treating the microbial infections and/or related diseases or conditions comprising an effective amount of the compounds and/or the derivatives thereof in the first aspect is also provided herein.

In one embodiment, said microbial infections are bacterial infections.

In another embodiment, said microbial infections comprise staphylococcal infections.

In other embodiment, the composition further comprises a pharmaceutically acceptable carrier, salt, ester, expicient, vehicle, prodrug, solvent, and diluent, or any combination thereof.

In a second aspect, the present invention provides methods for preventing and/or treating the microbial infections and/or related diseases or conditions including administering to a subject a composition comprising an effective amount of one or more compounds of Formula (I):

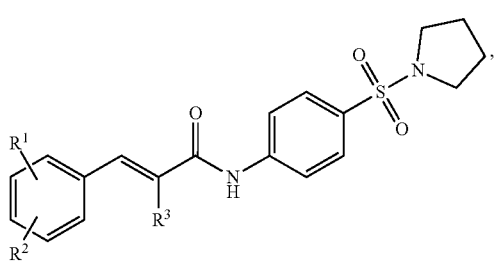

where $R^1$, $R^2$, and $R^3$ can independently or jointly be selected from the group: H; F; Cl; Br; I; OH; CN; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers thereof alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid (—$SO_3H$); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (=O); ether (—$OR^4$); and ester (—$COOR^5$ and —$OC(=O)R^5$);

where $R^1$ and $R^2$ can be bonded together to form a four-, five-, or six-membered heterocyclyl, cycloalkenyl, or cycloalkyl; and where $R^4$ and $R^5$ can be independently or jointly selected from the group consisting of: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl. Optionally, $R^1$ and $R^2$ are independently or jointly selected from

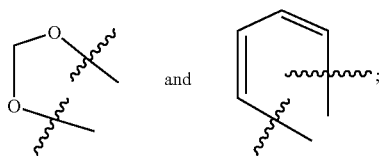 [SMILES: *OCO* ; */C=C\C=C/*]

$R^3$ is H or methyl.

In one embodiment, the microbial infections are bacterial infection.

In another embodiment, the microbial infections comprise Staphylococcal infections.

In other embodiment, the microbial infections and/or related diseases or conditions are caused by *Staphylococci* sp.

In yet another embodiment, the *Staphylococci* sp. comprise *Staphylococcus aureus* (*S. aureus*).

In still another embodiment, *S. aureus* comprise methicillin-resistant *S. aureus* (MRSA).

In other embodiment, the microbial infections and/or related diseases or conditions comprise infections of the skin and soft tissue, bone and joint, surgical wound, indwelling devices, lung and heart valves.

In certain embodiments, the present method further comprises reducing virulence of bacteria causing the microbial infections and/or related disease or conditions.

In some other embodiments, the present method further comprises inhibiting biosynthesis of staphyloxanthin in said bacteria and/or inhibiting or reducing production of pigments that are resistant to the bacterial host's immune defenses.

In another embodiment, said subject or bacterial host is a mammal.

In other embodiment, said subject or bacterial host is human.

BRIEF DESCRIPTION OF THE DRAWINGS

The patent of application file contains at least one drawing executed in color. Copies of this patent or patent application publication with color drawing(s) will be provided by the office upon request and payment of the necessary fee.

In the following detailed description, reference is made to the accompanying figures, depicting exemplary, non-limiting and non-exhaustive embodiments of the invention. So that the manner in which the above recited features of the present invention can be understood in detail, a more particular description of the invention, briefly summarized above, can be had by reference to the embodiments, some of which are illustrated in the appended figures. It should be noted, however, that the figures illustrate only typical embodiments of this invention and are therefore not to be considered limiting of its scope, for the invention can admit to other equally effective embodiments.

FIG. 1A shows the inhibition of wild-type (WT) *S. aureus* pigmentation using increasing concentrations of NP16; FIG. 1B shows the pigment inhibition by NP16; the $IC_{50}$ for pigment formation is ~300 nM; FIG. 1C depicts the chemical structure of compound NP16; FIG. 1D shows the growth curve of *S. aureus* COL in the presence of different concentrations of NP16. All data represent mean values±SD.

FIG. 2A depicts the cytotoxic activity of compound NP16 on MDCK cells; FIG. 2B shows the increased susceptibility of the NP16-treated *S. aureus* COL strain to killing by hydrogen peroxide; FIG. 2C shows the increased susceptibility of the NP16-treated *S. aureus* COL to killing by neutrophils; FIG. 2D is the UV spectrum of carotenoids extracted from different strains, with or without NP16 treatment. All data represent mean values±SD (*P<0.001; **P<0.0001). P values were determined using GraphPad Prism using an unpaired parametric t test with Welch's correction.

FIGS. 3A and 3B show the bacteria recovered from the livers and spleens, respectively, of mice infected with the wild-type COL or COL-ΔcrtN strains; FIGS. 3C and 3D show the bacteria recovered from the livers and spleens, respectively, of mice infected with the COL strain, with or without compound NP16 treatment; FIG. 3E shows the bacteria recovered from the kidneys of mice infected with clinical isolate strain AE052 or AE052-ΔcrtN; FIG. 3F shows the bacteria recovered from the kidneys of mice infected with strain AE052, with or without compound NP16 treatment. All data represent mean values±SEM (*P<0.05; P<0.01; *P<0.001). P values were determined using GraphPad Prism using an unpaired parametric t test with Welch's correction.

DETAILED DESCRIPTION OF THE INVENTION

Figure 1A:
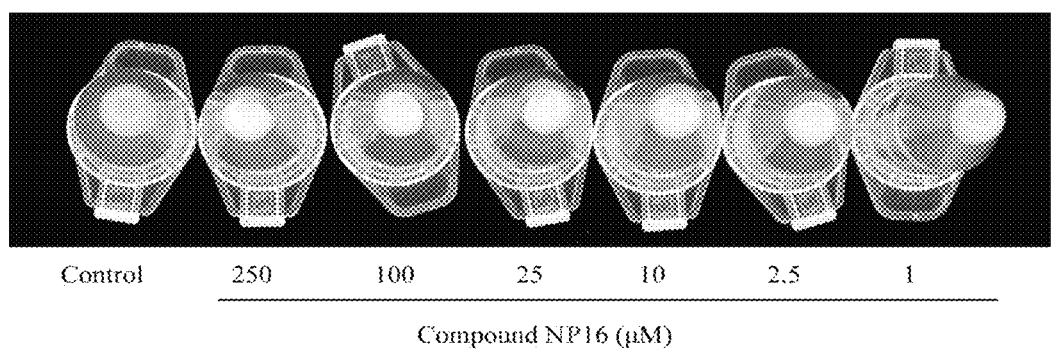
FIGS. 1A-1D show the in vitro pigment inhibition by compound NP16.

Following an established screening method for finding agents that reduce *Staphyloccous aureus* pigmentation [7], it is identified that the present compounds, termed NP16 and its derivatives, have block pigment production in *S. aureus* by targeting the 4,4-diapophytoene desaturase (CrtN). CrtN is proposed as a novel target for anti-virulence treatments in *S. aureus*. *S. aureus* staphyloxanthin contributes substantially to pathogenesis by interfering with host immune clearance mechanisms, but has little impact on ex vivo survival of the bacteria. Without wanting to be bound by theory, it is provided that agents blocking staphyloxanthin production may discourage the establishment and maintenance of bacterial infection without exerting selective pressure for antimicrobial resistance.

NP16 and its derivatives can be represented by Formula (I):

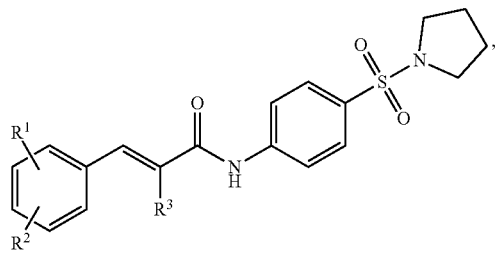

where $R^1$, $R^2$, and $R^3$ can independently or jointly be selected from the group: H; F; Cl; Br; I; OH; CN; $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers thereof; alkynyl; aralkyl; alkaryl; halogenated alkyl; heteroalkyl; aryl; heterocyclyl; cycloalkyl; cycloalkenyl; cycloalkynyl; hydroxyalkyl; aminoalkyl; amino; alkylamino; arylamino; dialkylamino; alkylarylamino; diarylamino; acylamino; hydroxyl; thiol; thioalkyl; alkoxy; alkylthio; alkoxyalkyl; aryloxy; arylalkoxy; acyloxy; nitro; carbamoyl; trifluoromethyl; phenoxy; benzyloxy; phosphonic acid; phosphate ester; sulfonic acid (—SO₃H); sulfonate ester; sulfonamide; alkaryl; arylalkyl; carbamate; amino; alkylamino; arylamino; dialkylamino; alkylarylamino; diarylamino; alkylthio; heteroalkyl; alkyltriphenylphosphonium; heterocyclyl; ketone (═O); ether (—OR⁴); and ester (—COOR⁵ and —OC(═O)R⁵);

where $R^1$ and $R^2$ can be bonded together to form a four-, five-, or six-membered heterocyclyl, cycloalkenyl, or cycloalkyl, such as

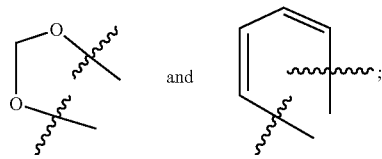 [SMILES: *OCO* ; */C=C\C=C/*]

$R^3$ is H or methyl; and where $R^4$ and $R^5$ can be independently or jointly selected from the group: a $(C_{1-4})$alkyl, such as methyl, ethyl, n-propyl, isopropyl, n-butyl, sec-butyl, isobutyl, tert-butyl; $(C_{2-4})$alkenyl, such as ethenyl, propenyl, butenyl, where the double bond can be located at any position in the alkenyl carbon chain, and including any alkenyl conformational isomers; and alkynyl.

The compounds of Formula (I) can include, but are not limited to, those compounds listed in Table 1.

TABLE 1

Compounds Blocking Staphyloxanthin Production

| Compound | Name | Structure |
| --- | --- | --- |
| 1 (NP16) | 3-phenyl-N-[4-(1-pyrrolidinylsulfonyl)phenyl]acrylamide | 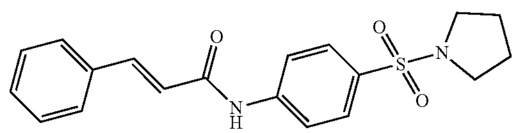 [SMILES: O=C(/C=C/c1ccccc1)Nc1ccc(S(=O)(=O)N2CCCC2)cc1] |

TABLE 1-continued

Compounds Blocking Staphyloxanthin Production

| Compound | Name | Structure |
|---|---|---|
| 2 | 3-(1-naphthyl)-N-[4-(1-pyrrolidinylsulfonyl)phenyl]acrylamide | 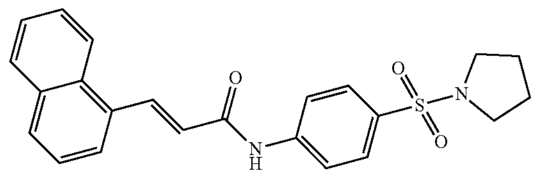 [SMILES: O=C(/C=C/c1cccc2ccccc12)Nc1ccc(S(=O)(=O)N2CCCC2)cc1] |
| 3 | 3-(1,3-benzodioxol-5-yl)-N-[4-(1-pyrrolidinylsulfonyl)phenyl]acrylamide | 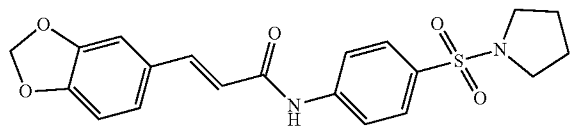 [SMILES: O=C(/C=C/c1ccc2c(c1)OCO2)Nc1ccc(S(=O)(=O)N2CCCC2)cc1] |
| 4 | 3-(2-chlorophenyl)-N-[4-(1-pyrrolidinylsulfonyl)phenyl]acrylamide | 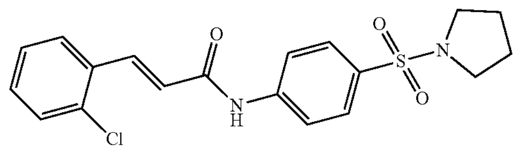 [SMILES: O=C(/C=C/c1ccccc1Cl)Nc1ccc(S(=O)(=O)N2CCCC2)cc1] |
| 5 | 3-(4-methoxyphenyl)-N-[4-(1-pyrrolidinylsulfonyl)phenyl]acrylamide | 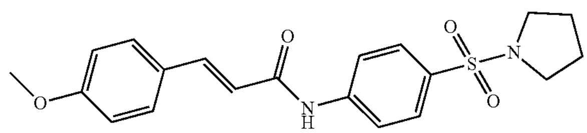 [SMILES: COc1ccc(/C=C/C(=O)Nc2ccc(S(=O)(=O)N3CCCC3)cc2)cc1] |
| 6 | 3-(2-nitrophenyl)-N-[4-(1-pyrrolidinylsulfonyl)phenyl]acrylamide | 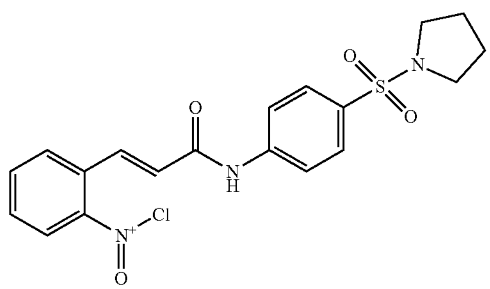 [SMILES: O=C(/C=C/c1ccccc1[N+](=O)Cl)Nc1ccc(S(=O)(=O)N2CCCC2)cc1] |
| 7 | 2-methyl-3-phenyl-N-[4-(1-pyrrolidinylsulfonyl)phenyl]acrylamide | 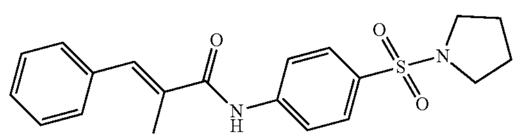 [SMILES: C/C(=C\c1ccccc1)C(=O)Nc1ccc(S(=O)(=O)N2CCCC2)cc1] |
| 8 | 3-(4-fluorophenyl)-N-[4-(1-pyrrolidinylsulfonyl)phenyl]acrylamide | 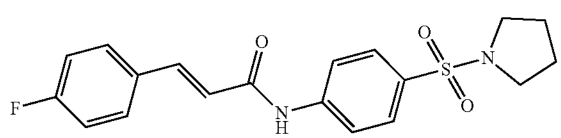 [SMILES: O=C(/C=C/c1ccc(F)cc1)Nc1ccc(S(=O)(=O)N2CCCC2)cc1] |
| 9 | 3-(3,4-dimethoxyphenyl)-N-[4-(1-pyrrolidinylsulfonyl)phenyl]acrylamide | 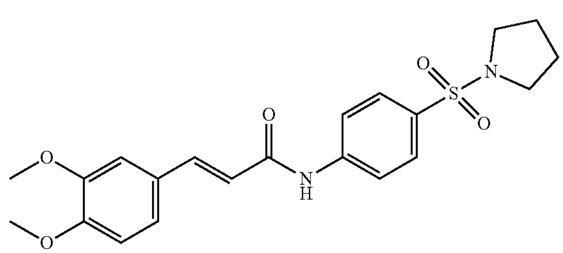 [SMILES: COc1ccc(/C=C/C(=O)Nc2ccc(S(=O)(=O)N3CCCC3)cc2)cc1OC] |

TABLE 1-continued

Compounds Blocking Staphyloxanthin Production

| Compound | Name | Structure |
|---|---|---|
| 10 | 3-(4-nitrophenyl)-N-[4-(1-pyrrolidinylsulfonyl)phenyl]acrylamide | 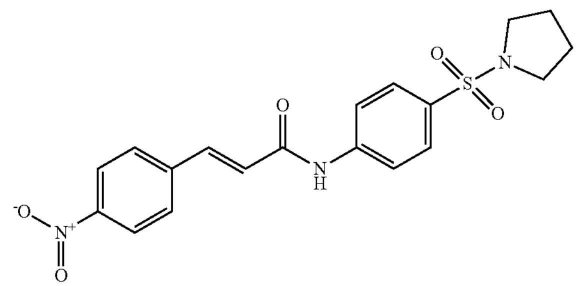 |
| 11 | 3-(5-bromophenyl)-N-[4-(1-pyrrolidinylsulfonyl)phenyl]acrylamide | 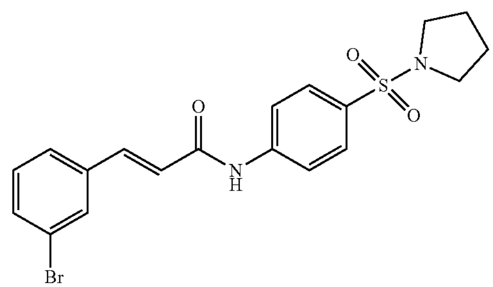 [SMILES: O=C(/C=C/c1cccc(Br)c1)Nc1ccc(S(=O)(=O)N2CCCC2)cc1] |
| 12 | 3-(6-bromophenyl)-N-[4-(1-pyrrolidinylsulfonyl)phenyl]acrylamide | 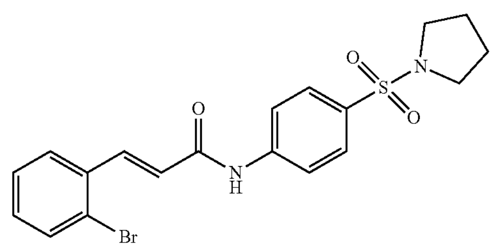 [SMILES: O=C(/C=C/c1ccccc1Br)Nc1ccc(S(=O)(=O)N2CCCC2)cc1] |
| 13 | 3-(4-bromophenyl)-N-[4-(1-pyrrolidinylsulfonyl)phenyl]acrylamide | 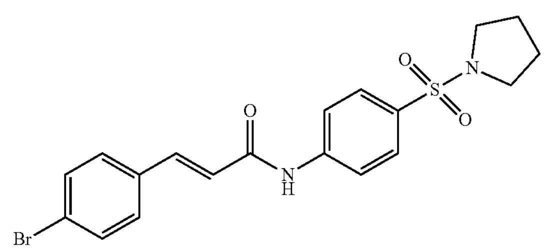 [SMILES: O=C(/C=C/c1ccc(Br)cc1)Nc1ccc(S(=O)(=O)N2CCCC2)cc1] |
| 14 | 3-(4-methylphenyl)-N-[4-(1-pyrrolidinylsulfonyl)phenyl]acrylamide | 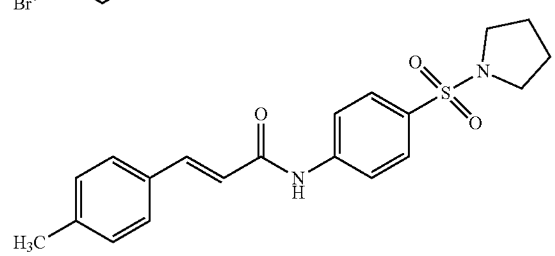 |
| 15 | 3-(6-methylphenyl)-N-[4-(1-pyrrolidinylsulfonyl)phenyl]acrylamide | 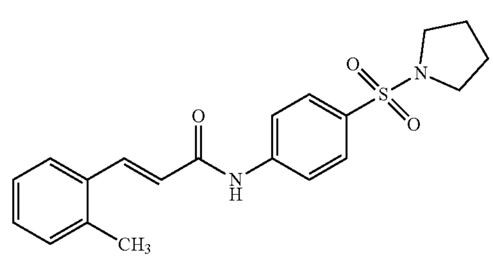 [SMILES: Cc1ccccc1/C=C/C(=O)Nc1ccc(S(=O)(=O)N2CCCC2)cc1] |

TABLE 1-continued

Compounds Blocking Staphyloxanthin Production

| Compound | Name | Structure |
|---|---|---|
| 16 | 3-(4-hydroxylphenyl)-N-[4-(1-pyrrolidinylsulfonyl)phenyl]acrylamide | 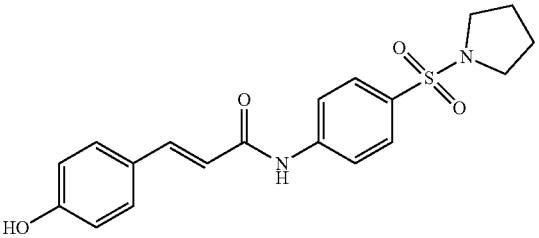 [SMILES: O=C(/C=C/c1ccc(O)cc1)Nc1ccc(S(=O)(=O)N2CCCC2)cc1] |
| 17 | 3-(5-acetoxylphenyl)-N-[4-(1-pyrrolidinylsulfonyl)phenyl]acrylamide | 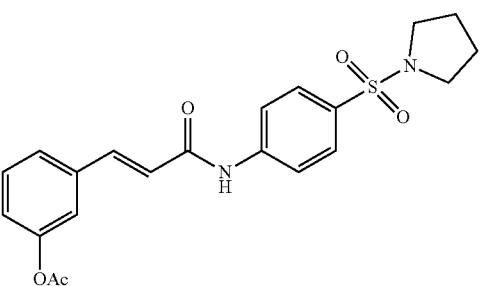 [SMILES: CC(=O)Oc1cccc(/C=C/C(=O)Nc2ccc(S(=O)(=O)N3CCCC3)cc2)c1] |
| 18 | 3-(6-acetoxylphenyl)-N-[4-(1-pyrrolidinylsulfonyl)phenyl]acrylamide | 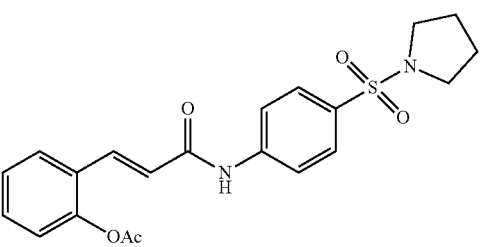 [SMILES: CC(=O)Oc1ccccc1/C=C/C(=O)Nc1ccc(S(=O)(=O)N2CCCC2)cc1] |
| 19 | 3-(4-acetoxylphenyl)-N-[4-(1-pyrrolidinylsulfonyl)phenyl]acrylamide | 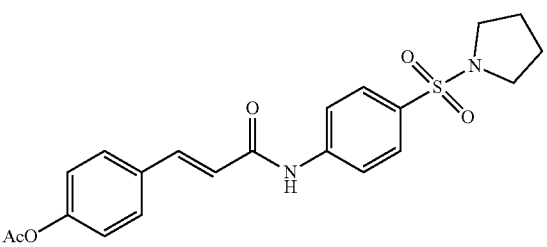 [SMILES: CC(=O)Oc1ccc(/C=C/C(=O)Nc2ccc(S(=O)(=O)N3CCCC3)cc2)cc1] |
| 20 | 3-(5-phenylphenyl)-N-[4-(1-pyrrolidinylsulfonyl)phenyl]acrylamide | 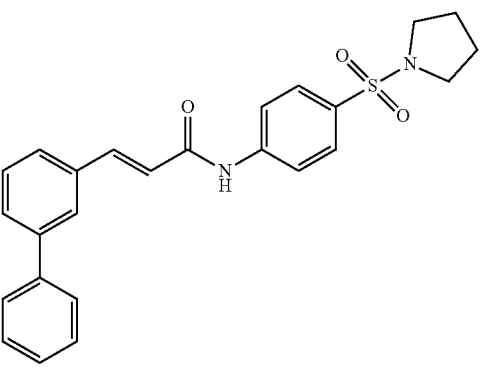 [SMILES: O=C(/C=C/c1cccc(-c2ccccc2)c1)Nc1ccc(S(=O)(=O)N2CCCC2)cc1] |

One or more compounds of Formula (I) can be combined and/or mixed with one or more of a pharmaceutically acceptable carrier, salt, ester, expicient, vehicle, prodrug, solvent, and diluent to make a composition.

As used herein, the phrase "pharmaceutically acceptable" can mean approved by a regulatory agency of the Federal or a state government or listed in the U.S. Pharmacopeia or other generally recognized pharmacopeia for use in animals and/or in humans.

As used herein, the term "carrier" can refer to a diluent, adjuvant, excipient, and/or vehicle with which the compound and/or antibiotic are administered. Such pharmaceutical carriers can be sterile liquids, such as water and oils, including those of petroleum, animal, vegetable or synthetic origin, such as peanut oil, soybean oil, mineral oil, sesame oil and the like.

As used herein, the phrase "pharmaceutically acceptable salt" can refer to derivatives of the compounds defined herein, wherein the parent compound is modified by making acid or base salts thereof.

The method of treating and/or preventing a microbial infection in a subject can include, but is not limited to, administering to a subject an effective amount of one or more compounds of Formula (I).

As used herein, the terms "treatment" or "treating" can refer to arresting or inhibiting, or attempting to arrest or inhibit, the development or progression of an infection and/or causing, or attempting to cause, the reduction, suppression, regression, or remission of an infection and/or a symptom thereof. As would be understood by those skilled in the art, various clinical and scientific methodologies and assays may be used to assess the development or progression of an infection, and similarly, various clinical and scientific methodologies and assays may be used to assess the reduction, regression, or remission of an infection or its symptoms. "Treatment" refers to both therapeutic treatment and prophylactic or preventative measures. Those in need of treatment include those already with the infection as well as those prone to have the infection or those in whom the infection is to be prevented. In at least some forms, the infection being treated can include, but is not limited to, *Staphylococcus aureus* infection. In other forms, the infection being treated is a microbial infection.

The administration can include, but is not limited to: administration though oral pathways, which administration includes administration in capsule, tablet, granule, spray, syrup, or other such forms; administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as administration topically; and administration via controlled released formulations, depot formulations, and infusion pump delivery.

For intravenous administration, the compounds can be packaged in solutions of sterile isotonic aqueous buffer to make the composition. When necessary, the composition can also include a solubilizing agent. The composition of the compounds can be supplied either separately or mixed together in unit dosage form, for example, as a dry lyophilized powder or concentrated solution in a hermetically sealed container such as an ampoule or sachette indicating the amount of active agent. If the compound is to be administered by infusion, it can be dispensed with an infusion bottle containing sterile pharmaceutical grade water or saline. When the compound is administered by injection, an ampoule of sterile water or saline can be provided so that the ingredients may be mixed prior to injection.

As used herein, the term "subject" can refer to an animal. Typically, the terms "subject" and "patient" may be used interchangeably herein in reference to a subject. As such, a "subject" can include a human that is being treated for a microbial infection as a patient.

As used herein, the term "animal" can refer to a mouse, rat, dog, cat, rabbit, pig, monkey, chimpanzee, and human.

As used herein, the terms "effective amount" and "therapeutically effective amount," can be used interchangeably, as applied to the compounds, antibiotics, and pharmaceutical compositions described can mean the quantity necessary to render the desired therapeutic result. For example, an effective amount is a level effective to treat, cure, or alleviate the symptoms of an infection for which the composition and/or antibiotic, or pharmaceutical composition, is/are being administered. Amounts effective for the particular therapeutic goal sought will depend upon a variety of factors including the infection being treated and its severity and/or stage of development/progression; the bioavailability and activity of the specific compound and/or antibiotic, or pharmaceutical composition, used; the route or method of administration and introduction site on the subject; the rate of clearance of the specific composition and other pharmacokinetic properties; the duration of treatment; inoculation regimen; drugs used in combination or coincident with the specific composition; the age, body weight, sex, diet, physiology and general health of the subject being treated; and like factors well known to one of skill in the relevant scientific art. Some variation in dosage will necessarily occur depending upon the condition of the subject being treated, and the physician or other individual administering treatment will, in any event, determine the appropriate dosage for an individual patient. Furthermore, the therapeutic methods described would not only apply to treatment in a subject, but could be applied to cell cultures, organs, tissues, or individual cells in vivo, ex vivo or in vitro.

The term "hydrocarbyl" as used herein includes reference to a moiety consisting exclusively of hydrogen and carbon atoms; such a moiety may comprise an aliphatic and/or an aromatic moiety. The moiety may comprise 1, 2, 3, 4, 5, 6, 7, 8, 9, 10, 11, 12, 13, 14, 15, 16, 17, 18, 19 or 20 carbon atoms. Examples of hydrocarbyl groups include $C_{1-6}$ alkyl (e.g. $C_1$, $C_2$, $C_3$ or $C_4$ alkyl, for example methyl, ethyl, propyl, isopropyl, n-butyl, sec-butyl or tert-butyl); $C_{1-6}$ alkyl substituted by aryl (e.g. benzyl) or by cycloalkyl (e.g. cyclopropylmethyl); cycloalkyl (e.g. cyclopropyl, cyclobutyl, cyclopentyl or cyclohexyl); aryl (e.g. phenyl, naphthyl or fluorenyl) and the like.

The term "alkyl" as used herein includes reference to a straight or branched chain alkyl moiety having 1, 2, 3, 4, 5, 6, 7, 8, 9, 10, 11, 12, 13, 14, 15, 16, 17, 18, 19 or 20 carbon atoms. Examples of alkyl groups include "$C_{1-6}$ alkyl" and "$C_{2-10}$ alkyl". The term "$C_{1-6}$ alkyl" as used herein include reference to a straight or branched chain alkyl moiety having 1, 2, 3, 4, 5 or 6 carbon atoms. The term "$C_{2-10}$ alkyl" as used herein include reference to a straight or branched chain alkyl moiety having 1, 2, 3, 4, 5, 6, 7, 8, 9 or 10 carbon atoms. This term includes reference to groups such as methyl, ethyl, propyl (n-propyl or isopropyl), butyl (n-butyl, sec-butyl or tert-butyl), pentyl, hexyl and the like. In particular, the alkyl moiety may have 1, 2, 3, 4, 5 or 6 carbon atoms.

The terms "alkenyl" and "$C_{2-6}$ alkenyl" as used herein include reference to a straight or branched chain alkyl moiety having 2, 3, 4, 5 or 6 carbon atoms and having, in addition, at least one double bond, of either E or Z stereochemistry where applicable. This term includes reference to groups such as ethenyl, 2-propenyl, 1-butenyl, 2-butenyl, 3-butenyl, 1-pentenyl, 2-pentenyl, 3-pentenyl, 1-hexenyl, 2-hexenyl and 3-hexenyl and the like.

The terms "alkynyl" and "$C_{2-6}$ alkynyl" as used herein include reference to a straight or branched chain alkyl moiety having 2, 3, 4, 5 or 6 carbon atoms and having, in addition, at least one triple bond. This term includes reference to groups such as ethynyl, 1-propynyl, 2-propynyl, 1-butynyl, 2-butynyl, 3-butynyl, 1-pentynyl, 2-pentynyl, 3-pentynyl, 1-hexynyl, 2-hexynyl and 3-hexynyl and the like.

The terms "alkoxy" and "$C_{1-6}$ alkoxy" as used herein include reference to —O-alkyl, wherein alkyl is straight or branched chain and comprises 1, 2, 3, 4, 5 or 6 carbon atoms. In one class of embodiments, alkoxy has 1, 2, 3 or 4 carbon atoms. This term includes reference to groups such as methoxy, ethoxy, propoxy, isopropoxy, butoxy, tert-butoxy, pentoxy, hexoxy and the like.

The term "cycloalkyl" as used herein includes reference to an alicyclic moiety having 3, 4, 5, 6, 7 or 8 carbon atoms. The group may be a bridged or polycyclic ring system. More often cycloalkyl groups are monocyclic. This term includes reference to groups such as cyclopropyl, cyclobutyl, cyclopentyl, cyclohexyl, norbornyl, bicyclo[2.2.2]octyl and the like.

The term "aryl" as used herein includes reference to an aromatic ring system comprising 6, 7, 8, 9, 10, 11, 12, 13, 14, 15 or 16 ring carbon atoms. Aryl is often phenyl but may be a polycyclic ring system, having two or more rings, at least one of which is aromatic. This term includes reference to groups such as phenyl, naphthyl, fluorenyl, azulenyl, indenyl, anthryl and the like.

"Cyclic group" means a ring or ring system, which may be unsaturated or partially unsaturated but is usually saturated, typically containing 5 to 13 ring-forming atoms, for example a 5- or 6-membered ring. The ring or ring system may be substituted with one or more hydrocarbyl groups. Cyclic group includes carbocyclyl and heterocyclyl moeities.

The term "carbocyclyl" as used herein includes reference to a saturated (e.g. cycloalkyl) or unsaturated (e.g. aryl) ring moiety having 3, 4, 5, 6, 7, 8, 9, 10, 11, 12, 13, 14, 15 or 16 carbon ring atoms. In particular, carbocyclyl includes a 3- to 10-membered ring or ring system and, in particular, 5- or 6-membered rings, which may be saturated or unsaturated. The ring or ring system may be substituted with one or more hydrocarbyl groups. A carbocyclic moiety is, for example, selected from cyclopropyl, cyclobutyl, cyclopentyl, cyclohexyl, norbornyl, bicyclo[2.2.2]octyl, phenyl, naphthyl, fluorenyl, azulenyl, indenyl, anthryl and the like.

The term "heterocyclyl" as used herein includes reference to a saturated (e.g. heterocycloalkyl) or unsaturated (e.g. heteroaryl) heterocyclic ring moiety having from 3, 4, 5, 6, 7, 8, 9, 10, 11, 12, 13, 14, 15 or 16 ring atoms, at least one of which is selected from nitrogen, oxygen, phosphorus, silicon and sulphur. In particular, heterocyclyl includes a 3- to 10-membered ring or ring system and more particularly a 5- or 6-membered ring, which may be saturated or unsaturated. The ring or ring system may be substituted with one or more hydrocarbyl groups.

A heterocyclic moiety is, for example, selected from oxiranyl, azirinyl, 1,2-oxathiolanyl, imidazolyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, pyrrolizidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, especially thiomorpholino, indolizinyl, isoindolyl, 3H-indolyl, indolyl, benzimidazolyl, cumaryl, indazolyl, triazolyl, tetrazolyl, purinyl, 4/V-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazoiyl, β-carbolinyl, phenanthridinyl, acridinyl, perimidinyl, phenanthrolinyl, furazanyl, phenazinyl, phenothiazinyl, phenoxazinyl, chromenyl, isochromanyl, chromanyl and the like.

The term "heterocycloalkyl" as used herein includes reference to a saturated heterocyclic moiety having 3, 4, 5, 6 or 7 ring carbon atoms and 1, 2, 3, 4 or 5 ring heteroatoms selected from nitrogen, oxygen, phosphorus and sulphur. The group may be a polycyclic ring system but more often is monocyclic. This term includes reference to groups such as azetidinyl, pyrrolidinyl, tetrahydrofuranyl, piperidinyl, oxiranyl, pyrazolidinyl, imidazolyl, indolizidinyl, piperazinyl, thiazolidinyl, morpholinyl, thiomorpholinyl, quinolizidinyl and the like. The ring or ring system may be substituted with one or more hydrocarbyl groups.

The term "heteroaryl" as used herein includes reference to an aromatic heterocyclic ring system having 5, 6, 7, 8, 9, 10, 11, 12, 13, 14, 15 or 16 ring atoms, at least one of which is selected from nitrogen, oxygen and sulphur. The group may be a polycyclic ring system, having two or more rings, at least one of which is aromatic, but is more often monocyclic. The ring or ring system may be substituted with one or more hydrocarbyl groups. This term includes reference to groups such as pyrimidinyl, furanyl, benzo[b]thiophenyl, thiophenyl, pyrrolyl, imidazolyl, pyrrolidinyl, pyridinyl, benzo[b]furanyl, pyrazinyl, purinyl, indolyl, benzimidazolyl, quinolinyl, phenothiazinyl, triazinyl, phthalazinyl, 2H-chromenyl, oxazolyl, isoxazolyl, thiazolyl, isoindolyl, indazolyl, purinyl, isoquinolinyl, quinazolinyl, pteridinyl and the like.

The term "halogen" as used herein includes reference to F, Cl, Br or I.

The expression "halogen containing moiety" as used herein includes reference to a moiety comprising 1 to 30 plural valence atoms selected from carbon, nitrogen, oxygen and sulphur which moiety includes at least one halogen. The moiety may be hydrocarbyl for example $C_{1-6}$ alkyl or $C_{1-6}$ alkoxy, or carbocyclyl for example aryl.

The term "substituted" as used herein in reference to a moiety means that one or more, especially up to 5, more especially 1, 2 or 3, of the hydrogen atoms in said moiety are replaced independently of each other by the corresponding number of the described substituents. The term "optionally substituted" as used herein means substituted or un-substituted. It will, of course, be understood that substituents are only at positions where they are chemically possible, the person skilled in the art being able to decide (either experimentally or theoretically) without inappropriate effort whether a particular substitution is possible.

The term "enantiomer" as used herein means one of two stereoisomers that have mirror images of one another.

The term "racemate" as used herein means a mixture of equal amounts of enantiomers of a chiral molecule.

The term "diastereomer" as used herein means one of a class of stereoisomers that are not enantiomers, but that have different configurations at one or more of the equivalent chiral centers. Example of diasteromers are epimers that differ in configuration of only one chiral center.

The term "stereoisomer" as used herein means one of a class of isomeric molecules that have the same molecular formula and sequence of bonded atoms, but different three-dimensional orientations of their atoms in space.

The term "prodrug" as used herein refers to a medication that is administered as an inactive (or less than fully active) chemical derivative that is subsequently converted to an active pharmacological agent in the body, often through normal metabolic processes.

The term "independently" used herein refers to two or more moieties each selected from a list of atoms or groups, which means that the moieties may be the same or different. The identity of each moiety is therefore independent of the identities of the one or more other moieties.

The term "jointly" used herein refers to two or more moieties are identical selected from a list of atoms or groups. In other words, the identity of each moiety is therefore dependent of the identities of the one or more other moieties being referred to be "jointly" selected from the list of atoms or groups.

EXAMPLES

The examples and embodiments described herein are for illustrative purposes only and various modifications or changes in light thereof will be suggested to persons skilled in the art and are included within the spirit and purview of this application. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Bacteria, Mice, and Chemical Reagents

The strains of S. aureus and E. coli are listed in Table 2. BALB/c mice were purchased from Charles River Laboratories. S. aureus was propagated in Terrific broth (TB) or on TB agar (Life Technologies). Unless otherwise indicated, all experiments were performed with bacteria derived from light-protected S. aureus 36-48 h stationary phase cultures, the point at which pigmentation phenotypes were readily apparent.

TABLE 2

Strains

| Strains | Description | Source |
|---|---|---|
| E. coli | | |
| Rosetta (DE3) | Host strain for gene expression | Lab source |
| S. aureus | | |
| RN4220 | Intermediate cloning host | Lab source |
| COL | Laboratory strain | Lab source |
| AE052 | Clinical isolate | [8] |
| COL-ΔcrtN | COL with crtN gene replaced ermC cassette | This study |
| AE052-ΔcrtN | AE052 with crtN gene replaced with ermC cassette | This study |
| USA300 | CA-MRSA, USA300 FPR3757, ATCC BAA-1556 | ATCC |

Minimum Inhibitory Concentration (MIC) Tests

MIC was determined by inoculating $5 \times 10^4$ S. aureus cells in 100 µl BHI medium in 96-well plates with a serial dilution of antibiotics. The MIC was defined as the minimum concentration resulting in a cell density less than 0.05 OD at 620 nm, which corresponded to no visible growth, after incubating for 18 h at 37° C.

Evaluation of NP-16 Analogues in Staphyloxanthin Production

S. aureus was propagated in Brain Heart Infusion broth (BHI) or on BHI agar (Oxoid). The in vitro pigment inhibition studies were performed by S. aureus USA300 cultured in BHI with or without the presence of inhibitor compounds at 37° C. and 250 rpm for 36-48 hours. The bacteria were washed twice with PBS prior to the staphyloxanthin purification with methanol. The OD of the extracts were monitor at 450 nm using DTX880 multi-plate reader spectrophotometer (Beckman). The concentration range tested for the compounds were between 300 nM to 700 nM, and control groups were added with equal volume of DMSO.

Cytotoxicity Evaluation of NP16 in MDCK Cells

The cytotoxicity of NP16 in MDCK cells was evaluated by MTT (3-[4,5-dimethylthiazol-2-yl]-2,5-diphenyltetrazolium bromide) assay according to manufacturer's instructions. A toxic control (1%) SDS was included to ensure the MTT assay was effective. The highest concentration of NP16 that could be used was 500 µM due to solubility limitations. SigmaPlot 11.0 (SPSS, IL) was used for graph plotting. Experiments were repeated twice in triplicate.

The IC50 values were obtained by fitting the inhibition data to a normal dose-response curve in SigmaPlot (CA).

Cytotoxicity Evaluation of Other NP-16 Analogues in Raw 264.7 Cells

The cytotoxicity of NP-16 and some of it analogues in Raw 264.7 cells was also evaluated by MTT (3-[4,5-dimethylthiazol-2-yl]-2,5-diphenyltetrazolium bromide) assay according to manufacturer's instructions. A toxic control (1%) SDS was included to ensure the MTT assay was working properly. The highest concentration of NP-16 analogues used was 500 µM due to solubility limitations. SigmaPlot 11.0 (SPSS, IL) was used for graph plotting. Experiments were carried out in triplicate and repeated twice.

The cytotoxicity of NP-16 and some of it analogues was tested against Raw 264.7 cells, and the cell tolerance of each compounds were documented in Table 3. Along with the in vitro staphyloxanthin production of the NP-16 analogues were being tested, the compounds can exert staphyloxanthin production inhibition. The staphyloxanthin from the overnight-cultured bacteria were extracted with methanol and quantified in via spectrophotometry. The results were presented in relative ratio to NP-16 in both the inhibition ratio as well as the TC50 in Table 3 (compound/analogue numbers correspond to those listed in Table 1).

TABLE 3

| Compounds/Analogues | TC50 to Raw 264.7 cells | Relative ratio to NP16 based on inhibition ratio |
|---|---|---|
| 1 (NP16) | >200 | 1 |
| 11 | >200 | 1.03 |
| 12 | >200 | 2.35 |
| 13 | >200 | 0.25 |
| 14 | >200 | 0.83 |
| 15 | >200 | 1.73 |
| 16 | 75 | 0.33 |
| 17 | ~75 | 0.58 |
| 18 | ~150 | 0.35 |
| 19 | ~150 | 0.86 |
| 20 | >200 | 0.61 | crtN Expression, Purification and Enzymatic Assay

CrtN with a histidine-maltose binding protein (MBP) tag was overexpressed in E. coli Rosetta (DE3) cells. A 10 ml overnight culture was transferred into 1 L of LB medium supplemented with 100 μg/ml ampicillin. Induction was carried out with 1 mM IPTG for 12 hours at 16° C. at an OD of 0.6 at 600 nm. The cell lysate was loaded onto a Ni-NTA column, and CrtN was eluted using a 75-ml linear gradient of 0-0.4 M imidazole in 50 mM sodium phosphate buffer, with 400 mM sodium chloride, pH 6.6. The collected fractions were analysed by SDS-PAGE to confirm the peak for MBP-CrtN. The target peak fractions were concentrated and the buffer was exchanged to loading buffer without imidazole using a PD-10 column (GE Healthcare). The collected solution was treated with TEV protease at 4° C. overnight. The protein sample was applied to a maltose column, and the flow-through was collected as native CrtN protein. For enzyme assay, 10 μg of purified CrtN was incubated with 100 μl of 4,4'-diapophytoene liposomes (containing 5 nmol of 4,4'-diapophytoene), 150 μM FAD and buffer II (20 mM phosphate buffer pH 8.0, 100 mM NaCl) in a total volume of 660 μl at 37° C. for 2 h (standard assay). The reaction was stopped by adding 1 volume of $CHCl_3$:MeOH (2:1, v/v). Followed by mixing, the sample was centrifuged at 16,000 g for 10 min. The organic phase was dried for LC/MS analysis.

Isolation of Carotenoids

The substrate (4,4'-diapophytoene) and product (4,4'-diaponeurosporene) were extracted from strains COL-ΔcrtN and COL-ΔcrtOP. Carotenoids were extracted from cell pellets using 300 ml of methanol per liter of cultured bacteria pellet until all visible pigments were removed. After centrifugation (4° C. and 8,000 g), colored supernatants were pooled and concentrated to 50 ml using an EZ-2 Plus centrifugal evaporator (Genevac Inc., Gardiner, N.Y., USA). A sample was mixed with 100 ml of EtOAc and 200 ml of NaCl (2.5 M). The extract sample in the upper organic phase was collected, washed with same volume of distilled water, and dried using the EZ-2 Plus evaporator. Dried samples were ready for silica gel isolation or stored at −70° C. prior to analysis. For structural elucidation, carotenoids were identified using a combination of HPLC retention times, UV-visible absorption spectra, and mass fragmentation spectra. Mass fragmentation spectra were monitored using both negative and positive ion modes in a mass range of m/z 200-1000 on the Varian 1200L LC/MS system equipped with an atmospheric pressure chemical ionization interface.

Hydrogen Peroxide Susceptibility Assay

S. aureus was grown in BHI with or without NP16 (40 μM). After 2 days, bacteria were washed twice in PBS, diluted to a concentration of $1\times10^7$ CFUs per 100 μl reaction mixture in a 96-well plate. Hydrogen peroxide ($H_2O_2$) in PBS was added to a 440 mM final concentration, and the plate was incubated for 1 hr at 37° C. with shaking. The reaction was stopped by the addition of 1,000 U/ml of exogenous catalase (Sigma-Aldrich, St. Louis, Mo.), and bacterial viability was assessed by plating dilutions on BHI agar plates.

Bactericidal Activity of Polymorphonuclear Leukocytes

The killing of S. aureus by human polymorphonuclear leukocytes (PMNs) was determined as previously described [9], with some modifications. Briefly, PMNs ($10^6$) were mixed with ~$10^7$ opsonized S. aureus bacteria MOI=10 in 24-well tissue culture plates. After centrifuged at 380 g for 8 min, plates were incubated at 37° C. for up to 1.5 h. PMNs were lysed with saponin (20 min on ice) and plated on BHIA plates. The percent survival was calculated by normalized with time zero. Statistics were performed with the Student's t-test (GraphPad Prism).

Murine Model of Intraperitoneal Infection

Eight- to ten-week-old female BALB/c mice were injected intraperitoneally (i.p) with $4\times10^8$ CFUs of early stationary phase S. aureus COL. After 3 d, animals were euthanized, the liver and spleen were isolated, homogenized in PBS, and plated on to obtain viable counts. For the treatment study, mice were randomized into two groups at the start of the experiment and administered, i.p., either 0.35 mg of NP16 or PBS with 5% Tween-80 as a control, twice per day, starting on d −1 to d 2 (a total of eight doses for each). Intraperitoneal challenge with $4\times10^8$ CFUs of early stationary phases S. aureus COL was performed on d 0. The mice were sacrificed on d 3 for enumeration of bacterial CFUs in liver and spleen homogenates.

For the clinical isolate S. aureus strain AE052, all operations were similar to those used for the COL strain, except $10^8$ CFUs of early stationary phase bacteria were used in the infection model, and kidneys were collected for monitoring bacterial loads. Statistics were performed using the Student's t-test (GraphPad Prism).

Compound NP16 Reduces Pigment Production

Figure 1B:
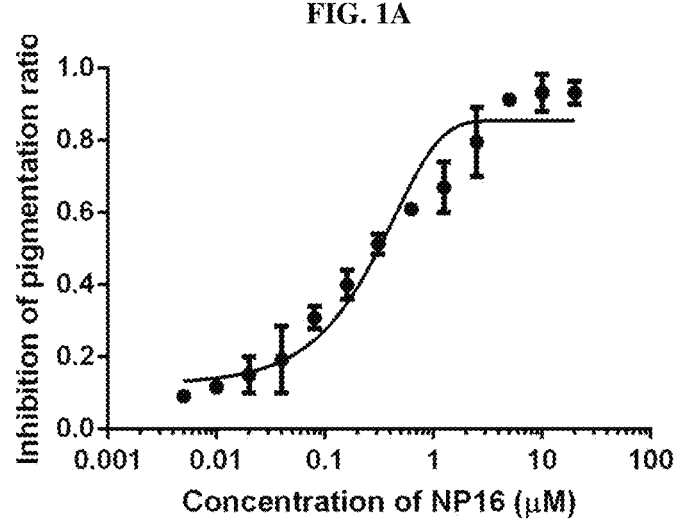
Figure 1C:
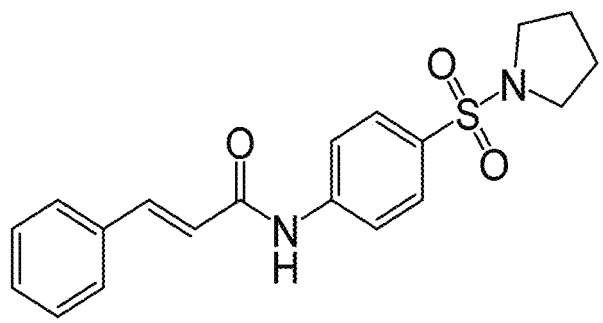
Figure 1D:
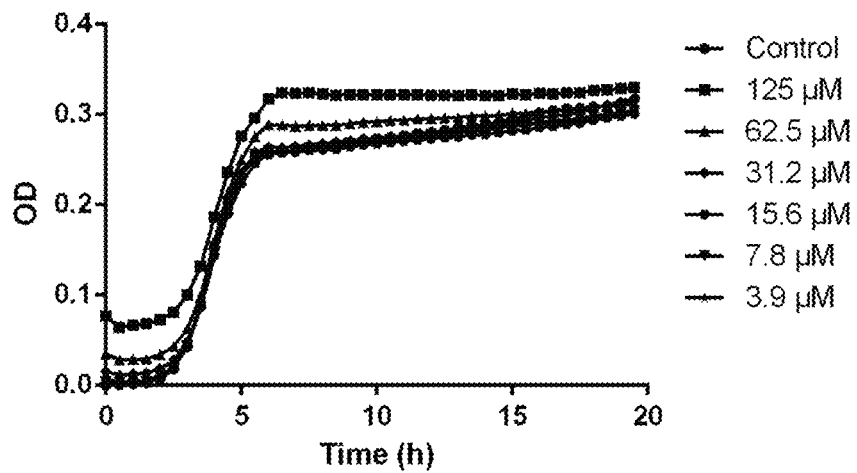

Compound NP16 (structure shown in FIG. 1C) had potent activity against S. aureus pigment formation in vitro, as shown in FIG. 1A, with $IC_{50}$ values ranging from 100 to 300 nM (FIG. 1B). In the biosynthesis of staphyloxanthin, the product of CrtN, 4,4'-diaponeurosporene, is a yellowish compound while products prior to CrtM catalysis are colorless. Thus, NP16 treatment is proposed to target CrtM or CrtN or other regulators that affect the expression of the crtOPQMN cluster, such as sigB or ispA [10]. The MIC of NP16 for USA300 was greater than 500 μM (FIG. 1D).

The functions of the five encoded enzymes were characterized by product analysis of gene deletion mutants. Firstly, in staphyloxanthin biosynthesis, two molecules of farnesyl diphosphate are condensed head-to-head to form dehydrosqualene (4,4'-diapophytoene), catalyzed by the dehydrosqualene synthase CrtM. Secondly, dehydrosqualene is dehydrogenated by the dehydrosqualene desaturase CrtN to form the yellow intermediate 4,4'-diaponeurosporene. Thirdly, oxidation of the terminal methyl group of 4,4'-diaponeurosporene is catalyzed by a mixed function oxidase CrtP, to form 4,4'-diaponeurosporenic acid. Then, glycosyl 4,4'-diaponeurosporenoate is formed by esterification of glucose at the C1″ position of 4,4'-diaponeurosporenic acid with CrtQ, a glycosyltransferase involved. Finally, glucose at the C6″ position is esterified with the carboxyl group of 12-methyltetradecanoic acid by the acyltransferase CrtO to yield staphyloxanthin. Staphyloxanthin was identified as β-D-glucopyranosyl 1-O-(4,4'-diaponeurosporen-4-oate)-6-O-(12-methyltetradecanoate).

Inhibition of CrtN by NP16 Results in $H_2O_2$ and Neutrophil Killing

Figure 2A:
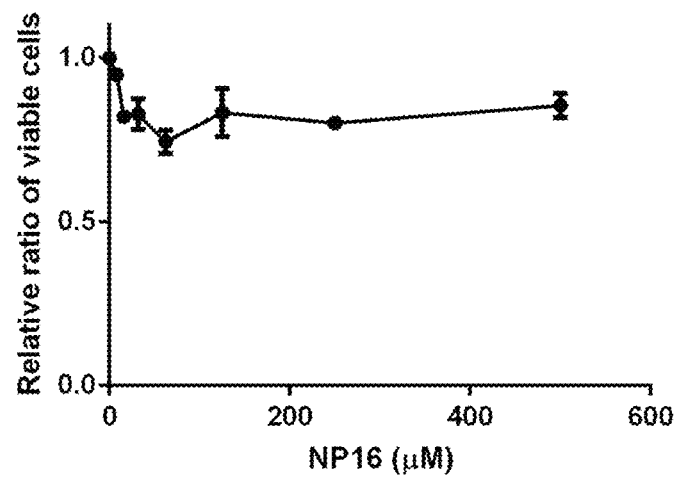
FIGS. 2A-2D show that NP16 treatment leads to increased sensitivity to oxidation and neutrophil killing.
Figure 2B:
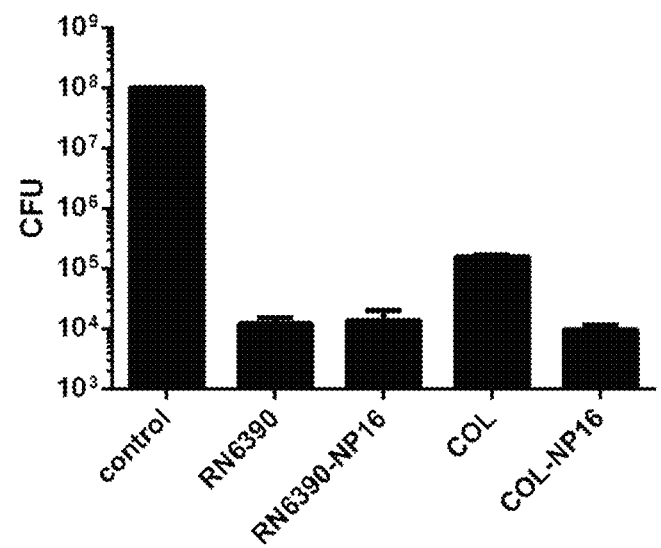

To probe the biological activities of CrtN, an isogenic crtN mutant in the COL strain via allelic replacement was generated. The mutation resulted in loss of yellow pigment. Compound NP16 had no effect on the growth of MDCK cells (FIG. 2A). A decrease in pigment production was found in S. aureus grown in the presence of this NP16 (FIG. 1A). Blocking S. aureus pigment formation has led to an increase in the susceptibility of the pathogen to hydrogen peroxide killing. For the non-pigmented strain RN6390, the susceptibility was similar irrespective of NP16 treatment (FIG. 2B). Additionally, as a carotenoid producing strain (FIG.

Figure 2C:
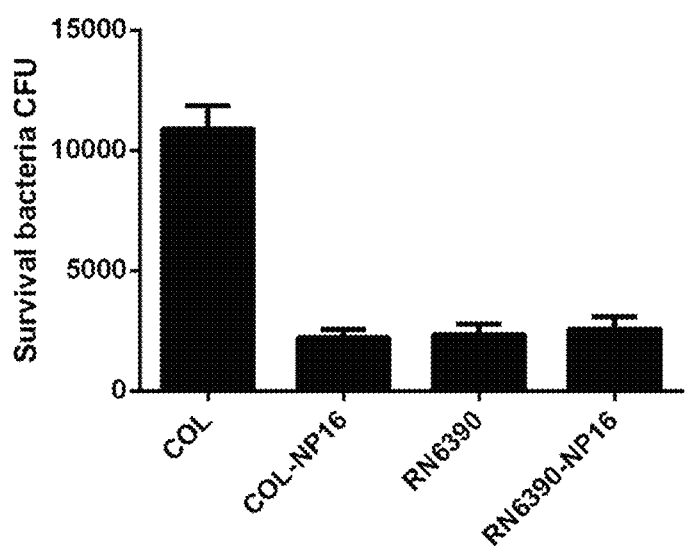
Figure 2D:
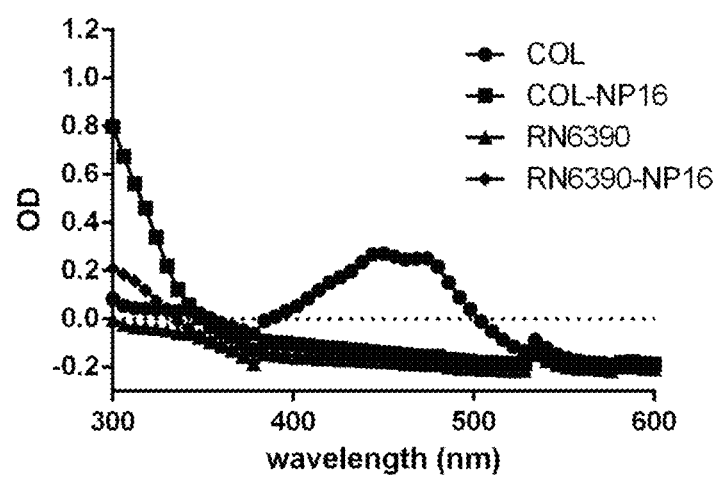

2D), COL survived significantly better than RN6390 and NP16-treated COL in human neutrophils (FIG. 2C).

Animal Studies

Figure 3A:
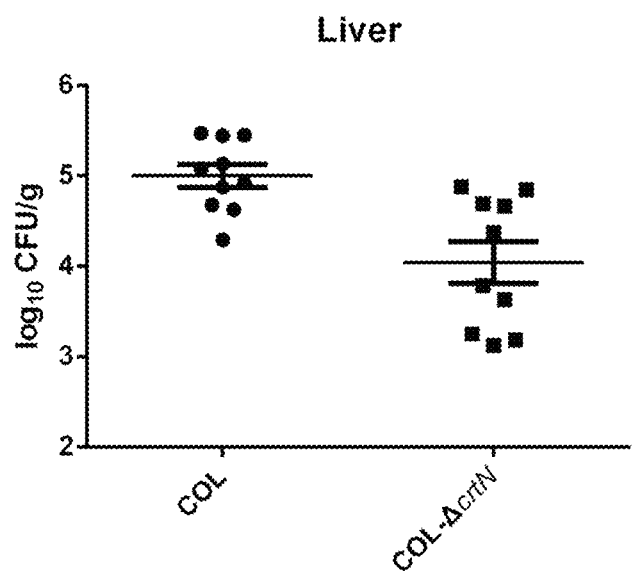
FIGS. 3A-3F show the in vivo effect of CrtN and its inhibition by NP16.
Figure 3B:
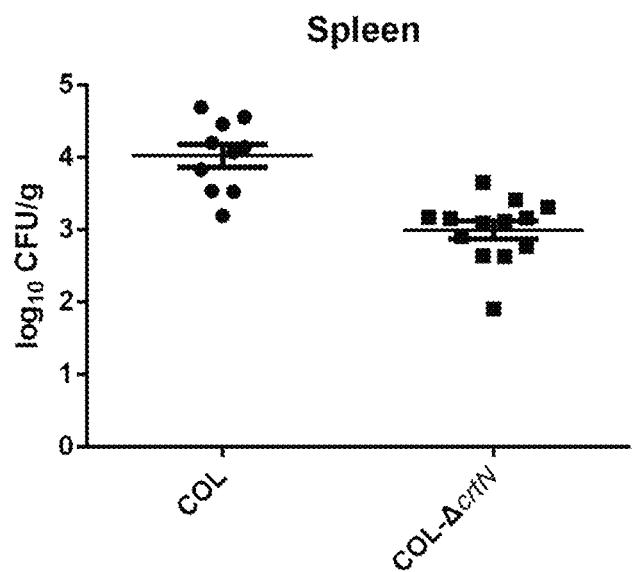

Using a systemic *S. aureus* infection model, the enzyme CrtM from *S. aureus* was identified to be a target for anti-infective therapy, based on virulence factor neutralization [3]. A similar model was applied to determine if crtN is also essential for infections in mice. The loss of staphyloxanthin reduced invasive disease potential, as mice inoculated with the isogenic *S. aureus* mutant COL-ΔcrtN showed lower bacterial population from the liver and spleen, compared with the $4 \times 10^8$ CFUs of wild-type *S. aureus* (by intraperitoneal injection), which led to a sustained infection (FIGS. 3a and 3b). Because the COL strain is a low virulence strain, no bacteria were detected in the kidneys from day 1 to day 3.

Another highly virulent clinical isolate, AE052, and its isogenic *S. aureus* mutant lacking the CrtN enzyme were also examined by these tests. Compared to wildtype strain, mutant strain in kidney was cleared by host after 72 hours post infection (FIG. 3E).

Figure 3C:
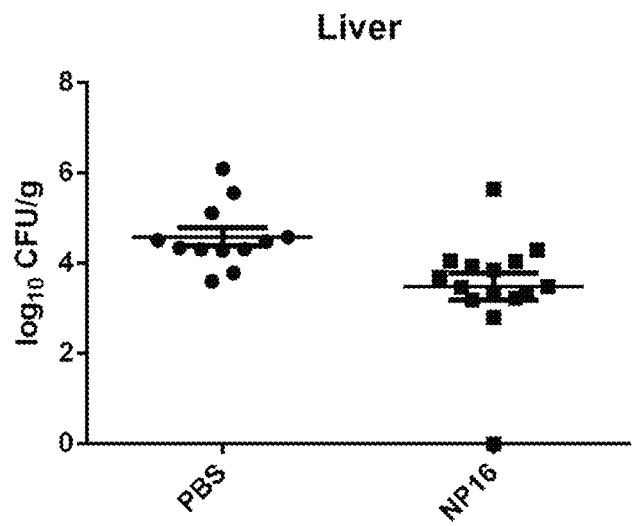
Figure 3D:
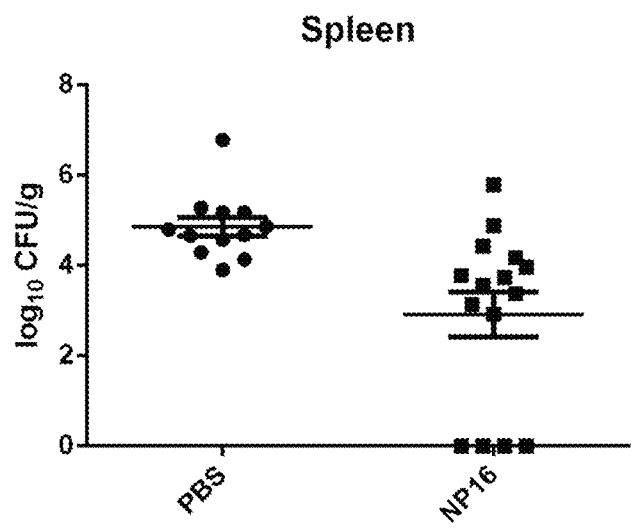
Figure 3E:
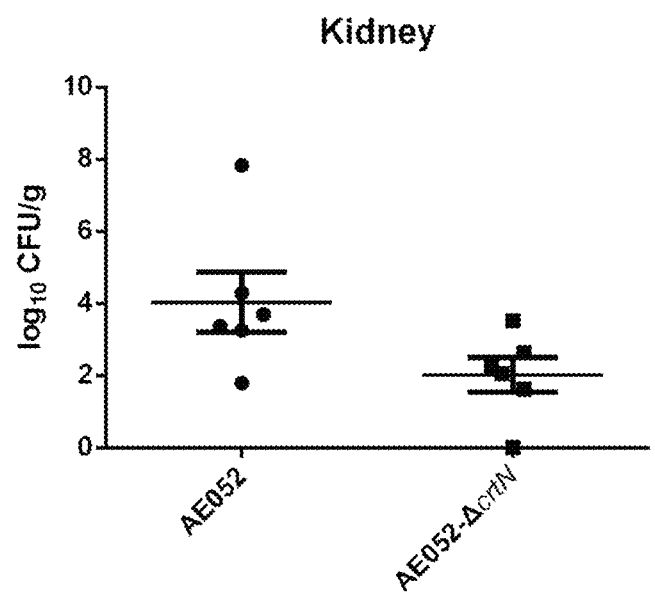
Figure 3F:
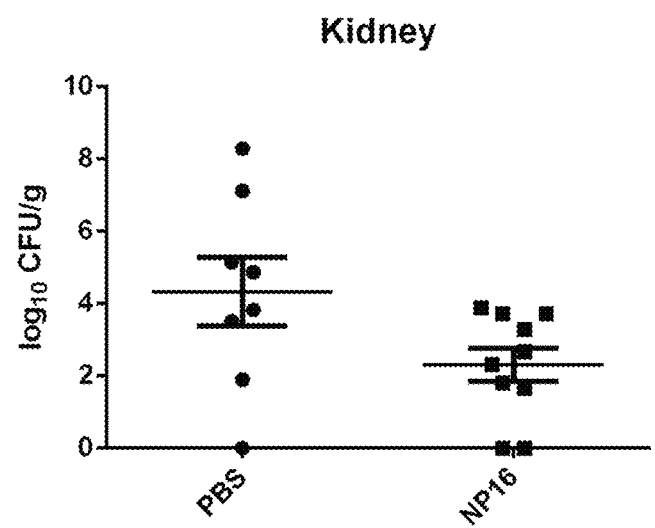

With the same intraperitoneal challenge used in FIGS. 3a, 3b and 3e, one group of mice (n=14) was treated with 0.35 mg of NP16 twice per day (days −1, 0, 1 and 2), and a second group (n=12) with a vehicle control. Upon sacrificing the mice at 72 hours, *S. aureus* COL bacterial counts in the livers and spleens of mice treated with compound NP16 were significantly lower than those of the control group (P<0.01) (FIGS. 3c and 3d). In the case of AE052 infections, bacterial counts in the kidneys of the mice (n=10 for both groups) treated with NP16 were significantly lower than those of the control group (P<0.001), with 6 of 10 below the detection threshold, versus only 2 of 10 in the control group (FIG. 3F). This result indicates a 98% decrease in surviving bacteria in the treatment groups infected with COL or AE052.

Discussion

It is identified that NP-16 is an inhibitor for CrtN and can exhibit anti-virulence effect on *S. aureus*. CrtM and CrtN are key enzymes in staphyloxanthin biosynthesis [11]. While staphyloxanthin plays a major role in *S. aureus* tolerance to host defence, it provides a basis for potential target for rational drug design for the use against *S. aureus*. It is proposed that a novel anti-infective drug without direct bactericidal properties, only targeting mechanisms that renders the pathogens susceptible to normal host innate immune clearance, is provided. As there is 30% sequence identity between the human SQS and the bacterial CrtM, and they share significant structural features. The presence of such homologue discouraged the employment of CrtM as druggable target this is further supported by a study focusing on the improvement of the specificity of BPH652 against CrtM was published recently [12]. Compared with CrtM, CrtN has no homologous enzyme in the human cholesterol biosynthesis pathway, making it an attractive drug target. A recently proposed CrtN inhibitor, nafitifine, is a topically administered antifungal compound [13], which has been shown to suppress chemotaxis, chemokinesis, chemiluminescence, and superoxide anion production of polymorphonuclear leukocytes at high concentrations [14]. The effects of naftifine are not stable in different organ (from no effect to reduced bacterial load for nearly 4 log) and inconsistency with CrtN mutant (always reduced bacterial load from 0.2 to 2 log at most). It is believed that this indicates that CrtN should not be the primary target of naftifine [6].

ROS are employed by phagocytic cells to eliminate bacteria. They are generated by nicotinamide adenine dinucleotide phosphate (NADPH) oxidase [15]. The bacterial carotenoids expressed by *S. aureus* may have a protective function against these defensive molecules [4, 16]. Evidence supported that a pigment-deficient *S. aureus* strain was more sensitive to oxidants, hydrogen peroxide and singlet oxygen, in vitro, as compared to a wild-type *S. aureus* strain [1]. Using intra-bacterial inhibition assay system, showed that the isogenic crtN mutant, which exhibited interrupted carotenoid synthesis, was more sensitive to purified human neutrophils. This confirmed the importance of CrtN in the intracellular survival of *S. aureus*.

CrtN inhibitors without direct bactericidal properties should possess theoretical advantages of not exerting a direct selective pressure on the pathogen or normal flora to develop drug resistance. Our approach, as well as other virulence factor-based concepts [3, 17] for highly specific anti-staphylococcal therapy relies mainly on the host normal innate immune response for pathogen clearance. Such strategies are much more ideal for clinical treatment and prophylactic applications with limited risk of developing drug resistant pathogen unlike the case observed with antibiotics.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

It should be understood that numerous specific details, relationships, and methods are set forth to provide a full understanding of the invention. One having ordinary skill in the relevant art, however, will readily recognize that the invention can be practiced without one or more of the specific details or practiced with other methods, protocols, reagents, cell lines and animals. The present invention is not limited by the illustrated ordering of acts or events, as some acts may occur in different orders and/or concurrently with other acts or events. Furthermore, not all illustrated acts, steps or events are required to implement a methodology in accordance with the present invention. Many of the techniques and procedures described, or referenced herein, are well understood and commonly employed using conventional methodology by those skilled in the art.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. It will be further understood that terms, such as those defined in commonly used dictionaries, should be interpreted as having a meaning that is consistent with their meaning in the context of the relevant art and/or as otherwise defined herein.

REFERENCE

The following references are incorporated herein by reference in their entirety:
1. Clauditz, A., et al., Staphyloxanthin plays a role in the fitness of *Staphylococcus aureus* and its ability to cope with oxidative stress. Infect Immun, 2006. 74(8): p. 4950-3.
2. Pelz, A., et al., Structure and biosynthesis of staphyloxanthin from *Staphylococcus aureus*. J Biol Chem, 2005. 280(37): p. 32493-8.
3. Liu, C. I., et al., A cholesterol biosynthesis inhibitor blocks *Staphylococcus aureus* virulence. Science, 2008. 319(5868): p. 1391-4.
4. Liu, G. Y., et al., *Staphylococcus aureus* golden pigment impairs neutrophil killing and promotes virulence through its antioxidant activity. J Exp Med, 2005. 202(2): p. 209-15.
5. Raisig, A. and G. Sandmann, 4,4'-diapophytoene desaturase: catalytic properties of an enzyme from the C(30) carotenoid pathway of *Staphylococcus aureus*. J Bacteriol, 1999. 181(19): p. 6184-7.
6. Chen, F., et al., Small-molecule targeting of a diapophytoene desaturase inhibits *S. aureus* virulence. Nat Chem Biol, 2016.
7. Sakai, K., et al., Search method for inhibitors of Staphyloxanthin production by methicillin-resistant *Staphylococcus aureus*. Biol Pharm Bull, 2012. 35(1): p. 48-53.
8. Ho, P. L., et al., Community-associated methicillin-resistant *Staphylococcus aureus* skin and soft tissue infections in Hong Kong. Hong Kong Med J, 2009. 15 Suppl 9: p. 9-11.
9. Kobayashi, S. D., et al., Bacterial pathogens modulate an apoptosis differentiation program in human neutrophils. Proc Natl Acad Sci USA, 2003. 100(19): p. 10948-53.
10. Lan, L., et al., Golden pigment production and virulence gene expression are affected by metabolisms in *Staphylococcus aureus*. J Bacteriol, 2010. 192(12): p. 3068-77.
11. Ku, B., et al., Preparation, characterization, and optimization of an in vitro C30 carotenoid pathway. Appl Environ Microbiol, 2005. 71(11): p. 6578-83.
12. Song, Y., et al., Phosphonosulfonates are potent, selective inhibitors of dehydrosqualene synthase and staphyloxanthin biosynthesis in *Staphylococcus aureus*. J Med Chem, 2009. 52(4): p. 976-88.
13. Favre, B. and N. S. Ryder, Characterization of squalene epoxidase activity from the dermatophyte Trichophyton rubrum and its inhibition by terbinafine and other antimycotic agents. Antimicrob Agents Chemother, 1996. 40(2): p. 443-7.
14. Vago, T., et al., Effects of naftifine and terbinafine, two allylamine antifungal drugs, on selected functions of human polymorphonuclear leukocytes. Antimicrob Agents Chemother, 1994. 38(11): p. 2605-11.
15. Fang, F. C., Antimicrobial reactive oxygen and nitrogen species: concepts and controversies. Nat Rev Microbiol, 2004. 2(10): p. 820-32.
16. Liu, G. Y., et al., Sword and shield: linked group B streptococcal beta-hemolysin/cytolysin and carotenoid pigment function to subvert host phagocyte defense. Proc Natl Acad Sci USA, 2004. 101(40): p. 14491-6.
17. Sully, E. K., et al., Selective chemical inhibition of agr quorum sensing in *Staphylococcus aureus* promotes host defense with minimal impact on resistance. PLoS Pathog, 2014. 10(6): p. e1004174.
18. Crossley, K. B., Staphylococci in human disease. 2nd ed. 2010, Chichester, West Sussex; Hoboken, N.J.: Wiley-Blackwell. xii, 623 p., 10 p. of plates.
19. Blot, S. I., et al., Outcome and attributable mortality in critically Ill patients with bacteremia involving methicillin-susceptible and methicillin-resistant *Staphylococcus aureus*. Arch Intern Med, 2002. 162(19): p. 2229-35.
20. Peng Gao, Julian Davies and Richard Yi Tsun Kao, "Dehydrosqualene desaturase as a novel target for antimicrobial therapeutics in *Staphylococcus aureus*", mBio, 8:e01224-17, (2017)

The invention claimed is:

1. A compound having one of the following formulae:

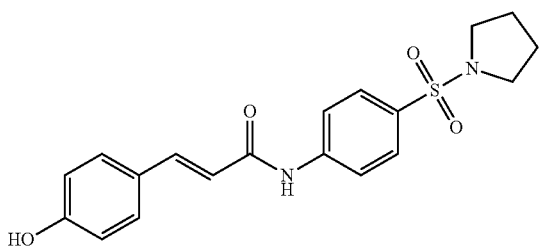

,

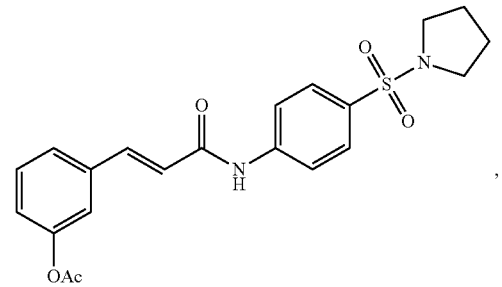

,

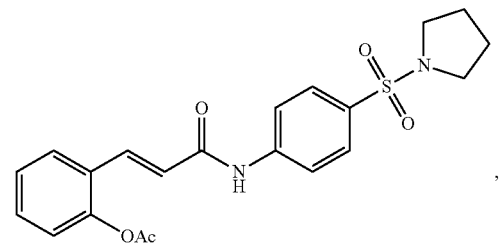

,

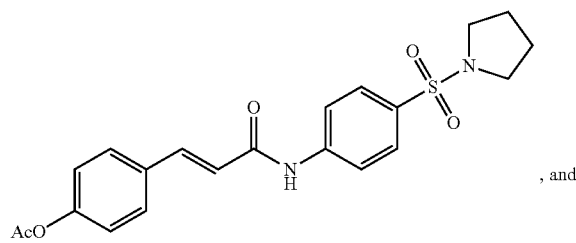

, and

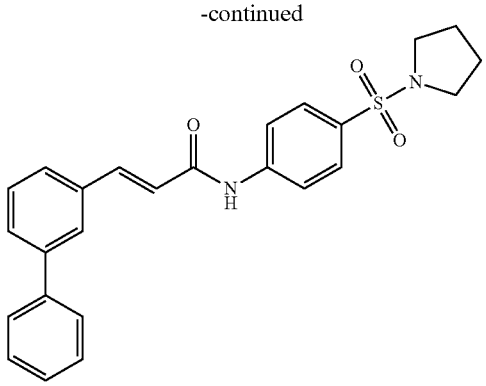

2. A composition comprising the compound according to claim 1 and a pharmaceutically acceptable carrier.

3. A method of treating and/or preventing microbial infections in a subject comprising:
   administering to said subject an effective amount of a compound of formula (I) or a derivative thereof:

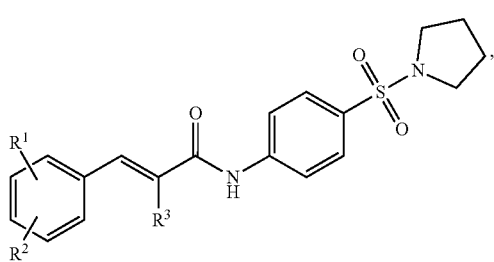

(I)

wherein $R^1$, $R^2$, and $R^3$ are independently or jointly selected from the group consisting of:
H; I; OH; CN; $(C_{1-4})$alkyl; $(C_{2-4})$alkenyl, wherein a double bond is optionally located at any position in the alkenyl carbon chain; alkynyl; aralkyl; alkaryl; halogenated alkyl; aryl; heterocyclyl; cycloalkyl; cycloalkenyl; cycloalkynyl; hydroxyalkyl; aminoalkyl; acylamino; thiol; thioalkyl; alkoxy; alkoxyalkyl; aryloxy; arylalkoxy; acyloxy; carbamoyl; trifluoromethyl; phenoxy; benzyloxy; phosphonic acid; phosphate ester; sulfonic acid (—$SO_3H$); sulfonate ester; sulfonamide; carbamate; alkyltriphenylphosphonium; ketone (═O); ether (—$OR^4$); ester (—$COOR^5$ and —$OC(═O)R^5$), and $R^1$ is not methyl at a C-2 position or a C-4 position in a cyclic group when $R^2$ and $R^3$ are both H,
wherein $R^1$, $R^2$, and $R^3$ are not jointly H; $R^3$ is not methyl when $R^1$ and $R^2$ are both H; $R^1$ and $R^2$ are not jointly —OMe, or
wherein $R^1$ $R^2$ are optionally bonded together to form a four-, five-, or six-membered heterocyclyl, cycloalkenyl, or cycloalkyl, and wherein $R^1$ and $R^2$ are not bonded together to form

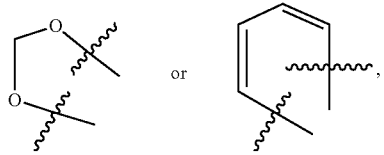 [SMILES: *OCO* ; */C=C\C=C/*]

and
wherein $R^4$ and $R^5$ are independently or jointly selected from the group consisting of: a $(C_{1-4})$alkyl; $(C_{2-4})$alkenyl, wherein a double bond is optionally located at any position in the alkenyl carbon chain; and alkynyl, and wherein $R^4$ is not methyl when $R^2$ and $R^3$ are both H.

4. The method of claim 3, wherein $R^3$ is H or methyl.

5. The method of claim 4, wherein the derivative is represented by one of the following formulae:

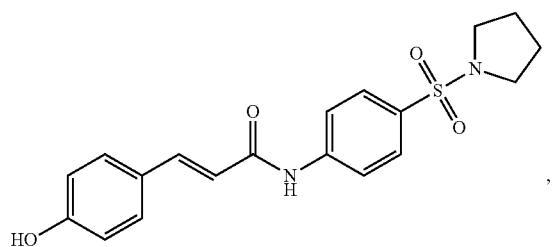

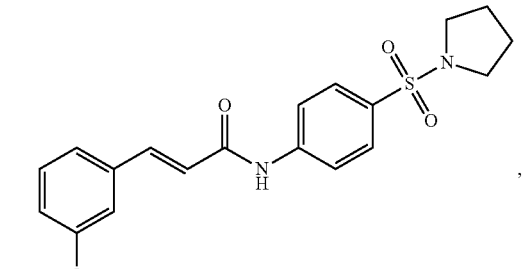

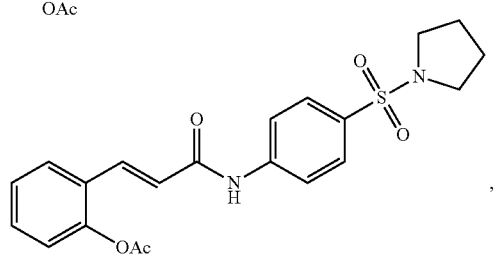

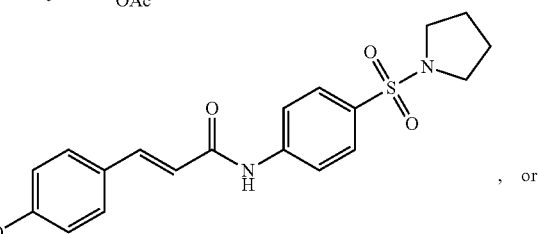

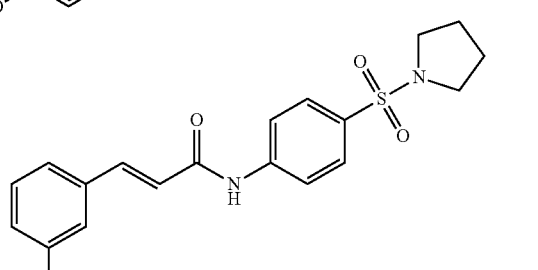

6. The method of claim 4, wherein the microbial infections comprise staphylococcal infection.

7. The method of claim 4, wherein the method reduces the production of pigment in *Staphylococcus aureus*.

8. The method of claim 4, wherein the microbial infections comprise infections of skin and soft tissue, infections of bone and joint, infections of surgical wound, infections of indwelling devices, or infections of lung and heart valves.

9. The method of claim 4, wherein the subject is a mammal.

10. The method of claim 4, wherein the subject is human or an animal.

* * * * *